(12) United States Patent
McKim et al.

(10) Patent No.: US 6,617,483 B1
(45) Date of Patent: Sep. 9, 2003

(54) POLYALKYLENE GLYCOL COMPOSITIONS FOR ENHANCED AROMATIC EXTRACTION

(75) Inventors: Artie S. McKim, Mandeville, LA (US); George Kvakovszky, Slidell, LA (US); Michael D. Donahue, The Woodlands, TX (US); Chris B. Watts, Mandeville, LA (US)

(73) Assignee: Gaylord Chemical Corporation, Slidell, LA (US)

( * ) Notice: Subject to any disclaimer, the term of this patent is extended or adjusted under 35 U.S.C. 154(b) by 0 days.

(21) Appl. No.: 09/565,170

(22) Filed: May 3, 2000

(51) Int. Cl.$^7$ .............................. C07C 7/10; C07C 7/17; C07C 7/00
(52) U.S. Cl. ................. 585/833; 585/856; 585/857; 585/860; 585/864; 585/865; 585/866
(58) Field of Search ................. 585/833, 856, 585/857, 860, 862, 864, 865, 866

(56) References Cited

U.S. PATENT DOCUMENTS

| | | | |
|---|---|---|---|
| 2,033,942 A | 3/1936 | Kurtz | 208/321 |
| 2,831,039 A | 4/1958 | Nevitt | 324/450 |
| 3,146,190 A | 8/1964 | Papadopoulos | 208/313 |
| 3,466,346 A | 9/1969 | DeGraff | 203/58 |
| 3,714,033 A | 1/1973 | Somekh et al. | 208/321 |
| 4,081,355 A | 3/1978 | Preusser et al. | 208/313 |
| 4,292,142 A | 9/1981 | Berg | 203/51 |
| 4,401,517 A | 8/1983 | Lee | 203/53 |
| 4,498,980 A | 2/1985 | Forte | 208/321 |
| 4,514,262 A * | 4/1985 | Berg | 203/51 |
| 4,676,872 A | 6/1987 | Berg et al. | 202/51 |
| 4,781,820 A | 11/1988 | Forte | 208/333 |
| 4,921,581 A | 5/1990 | Lee et al. | 203/56 |
| 4,948,470 A | 8/1990 | Lee | 203/51 |
| 5,022,981 A | 6/1991 | Forte | 208/334 |
| 5,032,232 A | 7/1991 | Lee et al. | 203/51 |
| 5,085,740 A | 2/1992 | Lee et al. | 203/51 |
| 5,139,651 A | 8/1992 | Forte | 208/334 |
| 5,310,480 A | 5/1994 | Vidueira | 208/313 |

FOREIGN PATENT DOCUMENTS

JP  358164525 A  *  9/1983

OTHER PUBLICATIONS

Lee, F.M., "Extractive Distillation: Separating Close Boiling Components," *Chemical Engineering*, vol. 105, p. 112–118 (Nov. 1990).
Sucksmith, "Extractive Distillation Saves Energy", *Chemical Engineering*, 91–95 (1982).
Maas, "Continuous Distillation: Separation of Binary Mixtures", *Handbook of Separation Techniques for Chemical Engineers*, Section 1.1, 3–57, (1979).
McCormick and Roche, "Continuous Distillation: Separation of Multicomponent MIxtures", *Handbook of Separation Techniques for Chemical Engineers*, Section 1.2, 59–145 (1979).
Seader and Kurtyka, *Perry's Chemical Engineers Handbook*, 6th Ed., 13, 53–57 (1984).
Wu, et al., "Improve Operation and Design of BTX Units", *Chemical Engineering*, 105, 139 (1998).
Barton, F.M., "Solubility Parameters" *Chemical Reviews*, 75(6), 731–753, (1975).
Barton, F.M., Handbook of Solubility Parameters and Other Cohesion Parameters, *CRC Press*, 94–110 and 153–161, (1983).
H. Burrell, "Solubility Parameter Values", *Interscience*, New York City, Section IV, 337–359 (1975).
Hansen, C.M., "The Three Dimensional Solubility Parameter–Key to Paint Component Affinities", *Journal of Paint Tech.* 39, 104–117 (1967).
"Jeffsol" Carbonates, Comparative Solvents Data, Huntsman Corporation, 2–7 (1995).

* cited by examiner

*Primary Examiner*—Walter D. Griffin
*Assistant Examiner*—Tam M. Nguyen
(74) *Attorney, Agent, or Firm*—Needle & Rosenberg, P.C.

(57) ABSTRACT

The invention relates to extractive distillation compositions for separating a mixture of hydrocarbon compounds, wherein the extractive distillation composition includes at least one alkylene glycol compound, and at least one compatibility agent, wherein the compatibility agent is selected from materials having polar parameters and hydrogen bonding parameters such that the extractive distillation composition provides improved separation of the hydrocarbon compounds, as compared to the use of the extractive distillation composition without the compatibility agent.

26 Claims, 3 Drawing Sheets

POLYALKYLENE GLYCOL COMPOSITIONS FOR ENHANCED AROMATIC EXTRACTION

FIELD OF THE INVENTION

This invention relates generally to extractive distillation processes and extractive distillation compositions for enhancing the separation of hydrocarbon compounds via extractive distillation.

BACKGROUND OF THE INVENTION

It is difficult to efficiently and economically separate mixtures of organic compounds having similar chemical characteristics, and nearly the same boiling point. Conventional fractional distillation can be expensive and inefficient in this situation, in that large and expensive columns are required, which have large numbers of plates, and utilize high reflux ratios, with correspondingly high energy consumption rates.

Extractive distillation is a technique for separating certain close boiling mixtures. In extractive distillation, a high boiling solvent is typically introduced into a distillation zone containing a lower boiling feed mixture that is to be separated. The high boiling solvent interacts with the feed mixture to effectively decrease the volatility of some feed mixture components, typically the more polar feed components, so that the less polar feed components can be separated as a vapor stream. The solvent and the more polar feed components typically exit the distillation zone as a heavy fraction. An extractive distillation process has been described in the article entitled "Extractive Distillation Saves Money" by Ian Sucksmith, Chemical Engineering, Jun. 18, 1982, pages 91–95. Other literature sources relating to continuous distillation techniques and/or extractive distillation techniques include Sections 1.1 and 1.2 of the "Handbook of Separation Techniques for Chemical Engineers", Phillip A Schweitzer Editor McGraw Hill Book Company, 1979, and Seader et. al. in Perry's Chemical Engineering Handbook, pages 13–53 to 13–57, McGraw-Hill Book company, 1984.

A variety of methods for employing extractive distillation to separate various classes of hydrocarbons, such as aromatic, olefins, or cycloalkanes, from other close-boiling hydrocarbons, such as paraffins, is known in the hydrocarbons industry. In particular, many refinery streams comprise "BTX" streams composed of close boiling mixtures of aliphatic hydrocarbons (such as isomers of heptane and octane) and aromatic hydrocarbons (such as benzene, toluene, and xylenes). It is known in the industry to use mixtures of solvents such as various polyethylene glycol ethers and water as solvents for extractive distillation of hydrocarbon and/or BTX streams (i.e. "Udex" processes, and variations thereof). U.S. Pat. Nos. 3,714,033 and 4,921,581 disclose the use of polyalkylene glycol solvents toward this end.

Since the institution of "Udex" technology, efforts have been made to improve its production efficiency and economic performance in hydrocarbon separations by the use of other types of solvents for extractive distillation. Morpholine derivatives and N-alkylpyrrolidones were disclosed as extractive distillation solvents, respectively, in U.S. Pat. Nos. 4,081,355 and 4,948,470. U.S. Pat. No 4,676,872 discloses the use of adiponitrile in combination with other materials such as ethylene carbonate, nitrobenzene, and certain dialkyl esters, for the separation of xylene isomers. U.S. Pat. No. 4,292,142 discloses the use of phthalic anhydride in combination with other materials such as isophorone, for the separation of ethylbenzene from xylenes.

Other known processes have employed organic sulfones as solvents in extractive distillation processes. U.S. Pat. Nos. 2,033,942 and 2,831,039 described the use of dialkyl sulfones, including dimethyl sulfone, in such separations. U.S. Pat. No. 4,401,517 relates to the use of $C_4$–$C_8$ sulfones as selective extractive distillation solvents. U.S. Pat. No. 3,146,190 described the use of sulfolane (tetramethylene sulfone) as a selective extraction solvent for the purification of pyrolysis fuels and catalytically reformed gasolines. U.S. Pat. No. 3,466,346 describes further refinements of sulfolane based extractive distillation processes.

Polyalkylene glycols or sulfolane are the most widely used extractive distillation solvents used in modern hydrocarbon processing. Both solvents exhibit reasonably high selectivity for separating aromatic materials from aliphatic compounds, but, Wu et. Al. estimate (Chemical Engineering, page 139, March 1998) that for a typical industrial BTX extraction unit, a 1% increase in aromatics recovery would result in savings of up to $100,000 per year. Such savings derive from both decreased need for capital investment, and decreased unit energy requirements (electricity, steam, etc.) needed to perform the extractive distillation. Polyalkylene glycols also suffer from significant thermal degradation on an annual basis, and therefore necessitate regular makeup of their volume, which incurs significant expense.

Relatively recent approaches to extraction medium modification involve the introduction of cosolvents to glycol extraction media, as a way of enhancing extraction performance. U.S. Pat. No. 5,139,651 discloses the use of polyalkylene glycols and a glycol ether cosolvent to extract aromatics. Such compositions are also described in U.S. Pat. Nos. 4,498,980 and 4,781,820. The use of sulfolane as a cosolvent in polyalkylene glycol solvent systems is described in U.S. Pat. No. 5,310,480. U.S. Pat. No. 5,085,740 discloses a ternary mixture composed of an N-alkyl-2-pyrrolidone, a sulfolane compound, and a glycol. U.S. Pat. No. 5,032,232 relates to mixtures of N-alkyl-2-thiopyrollidone with sulfolane and/or tetraethylene glycol, and their use in extractive distillation processes.

Thus, both technical and financial considerations provide a continuing need for developing novel and improved extractive distillation compositions which exhibit advantages (such as higher selectivity and/or capacity/loading) over known solvents for the extractive distillation of mixtures of close-boiling hydrocarbons.

SUMMARY OF THE INVENTION

The instant invention relates to improved extractive distillation compositions, and processes that employ the extractive distillation compositions.

In some aspects, the invention relates to extractive distillation compositions for separating a mixture of hydrocarbon compounds, wherein the extractive distillation composition includes at least one alkylene glycol compound, and at least one compatibility agent, wherein the compatibility agent is selected from materials having solubility parameters such that the extractive distillation composition provides improved separation of the hydrocarbon compounds, as compared to the use of the extractive distillation composition without the compatibility agent.

In other aspects, the invention relates to processes for separating hydrocarbon compounds of similar boiling points by extractive distillation, that employ the extractive distillation compositions of the invention.

Additional advantages of the invention will be set forth in part in the description that follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE PREFERRED EMBODIMENTS

Figure 1:
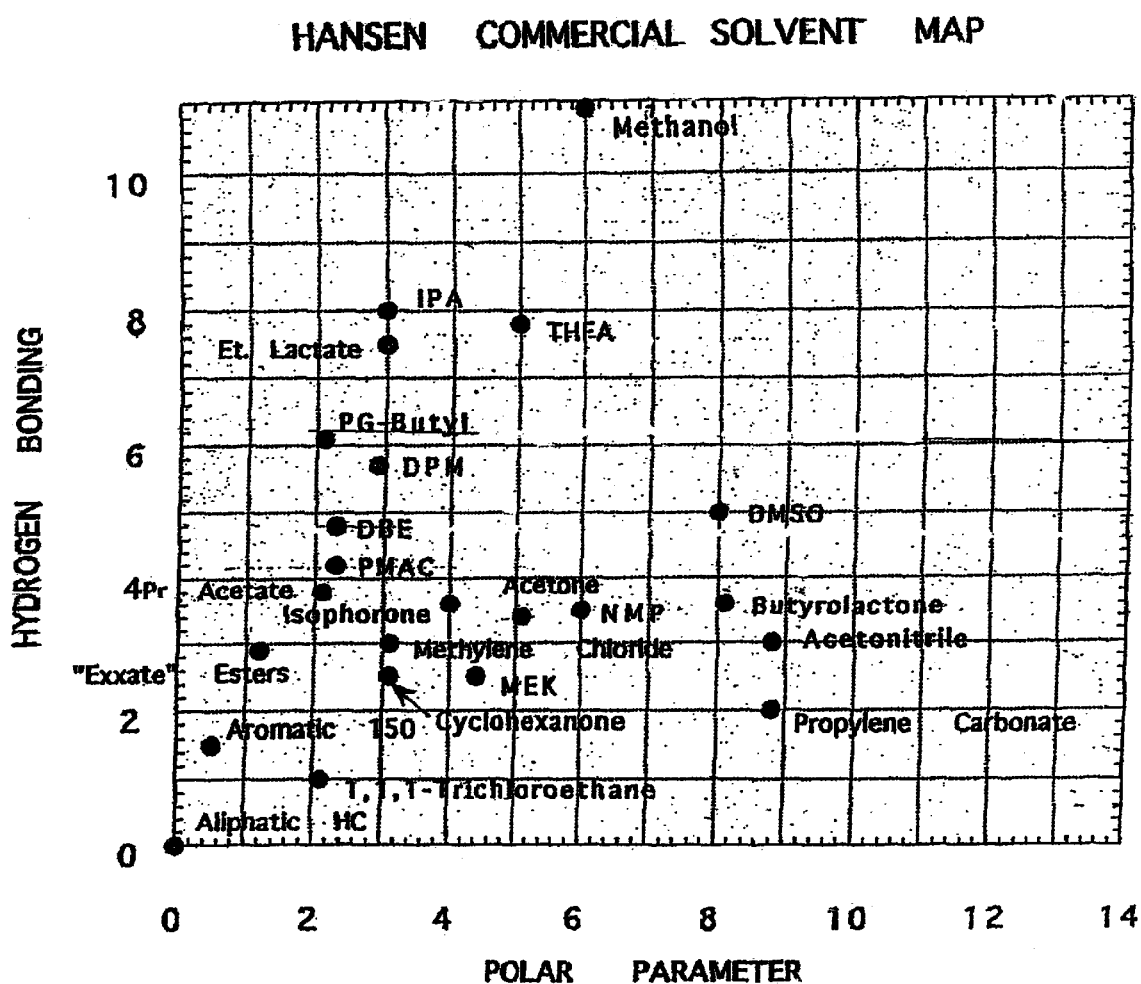
FIG. 1 shows a "map" of known Hansen's Solubility Hydrogen Bonding Parameters and Hansen's Solubility Polar Parameters for a number of readily available commercial solvents.

The present invention may be understood more readily by reference to the following detailed description of preferred embodiments of the invention and the examples included therein.

Before the present compounds, compositions, articles, devices and/or methods are disclosed and described, it is to be understood that unless otherwise specifically stated by the claims, this invention is not limited to specific synthetic methods, specific types of distillation or fractionation equipment, methods of operating the distillation or fractionation equipment, or to particular ranges of temperature or pressure, as such may, of course, vary. It is also to be understood that the terminology used herein is for the purpose of describing particular embodiments only and is not intended to be limiting.

It must be noted that, as used in the specification and the appended claims, the singular forms "a", "an" and "the" include plural referents unless the context clearly dictates otherwise. Thus, for example, reference to "an aromatic compound" includes mixtures of aromatic compounds, references to "a pharmaceutical carrier" includes mixtures of two or more such carriers, and the like.

Ranges may be expressed herein as from "about" one particular value, and/or to "about" another particular value. When such a range is expressed, another embodiment includes from the particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not. For example, the phrase "optionally substituted lower alkyl" means that the lower alkyl group may or may not be substituted and that the description includes both unsubstituted lower alkyl and lower alkyl when there is substitution.

References in the specification and concluding claims to parts by weight of a particular element or component in a composition or article denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5 and are present in such ratio regardless of whether additional components are contained in the compound.

A weight percent of a component, unless specifically stated to the contrary, is based on the total weight of the formulation or composition in which the component is included.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in a polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

The term "alkyl" as used herein refers to a branched or unbranched saturated hydrocarbon of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl, and the like. Preferred alkyl groups contain 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms.

The term "alkoxy" as used herein intends an alkyl group bound through a single, terminal ether linkage; that is, an "alkoxy" group may be defined as —OR where R is an alkyl as defined above. A "lower alkoxy" group intends an alkoxy group containing from one to six, more preferably from one to four, carbon atoms.

The term "alkylene" as used herein refers to a difunctional saturated branched or unbranched hydrocarbon chain, containing from 1 to 24 carbon atoms, and includes, for example, methylene (—$CH_2$—), ethylene (—$CH_2CH_2$—), propylene (—$CH_2CH_2CH_2$—), 2-methyl propylene [—$CH_2$—CH($CH_3$)—$CH_2$—], hexylene [—$(CH_2)_6$—] and the like. "Lower alkylene" refers to an alkylene group of from 1 to 6, more preferably from 1 to 4, carbon atoms. The term "cycloalkylene" as used herein refers to a cyclic alkylene group, typically a 5- or 6- membered ring.

The term "aliphatic" as used herein describes branched or unbranched hydrocarbon chains or groups containing from 1 to 24 carbon atoms which are saturated, i.e., they have no double bonds between the carbon atoms.

The term "aromatic" as used herein describes substituted or unsubstituted benzene-like compounds of six to twenty five carbon atoms having at least one 6-membered ring residue of carbon atoms, with alternating (conjugated) double bonds which have (4n+2)π electrons, wherein n is a positive integer.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount". However, an appropriate effective amount may be determined by one of ordinary skill in the art using only routine experimentation.

Reference will now be made in detail to the present preferred embodiment(s) of the invention. As discussed above, one aspect of the present invention relates to improved extractive distillation compositions for separating a mixture of hydrocarbon compounds. The extractive distillation compositions of this invention are characterized by enhanced selectivity and/or high capacity for the separation of mixtures of hydrocarbon compounds, and by enhanced thermal stability, relative to extractive solvents currently available to refinery science.

In one embodiment, the extractive distillation compositions for separating a mixture of hydrocarbon compounds comprise:

a) at least one akylene glycol compound, and
b) at least one compatibility agent.

It is to be understood that the at least one alkylene glycol compound and the at least one compatibility agent may be separately supplied to the extractive distillation processes of the invention, although they are often supplied as a mixture. It is to be understood that a mixture two or more alkylene glycol compounds may be employed, and that a mixture of two or more compatibility agents may be employed.

The alkylene glycol compounds employed in the extractive distillation compositions of the invention include organic alcohol compounds having at least two hydroxyl groups, and at least one alkylene residue. The alkylene glycol compound may additionally comprise ether groups, and/or additional alkylene residues, which may or may not have the same structure as the original alkylene groups. The alkylene glycol compounds may also comprise additional alkyl, alkoxy, aromatic, or herteroaromatic residues. Examples of suitable alkylene glycol compounds include ethylene glycol, trimethylene glycol, propylene glycol, glycerol, 1,2-butylene glycol, 1,4-butanediol, 1,6-hexanediol, dipropylene glycol, tripropylene glycol, trimethylol ethane, trimetholpropane, and the like.

In preferred embodiments of the invention, the alkylene glycol compounds of the invention are polyalkylene glycol compounds of the formula:

HO—[CHR$_1$(CR$_2$R$_3$)$_n$—O]$_m$—H wherein n is an integer from 1 to 5, and m is an integer having a value of 1 or greater. Preferably n is 1,2 or 3; and m is between about 2 to about 20. More preferably, m is from about 3 to about 8. R$_1$, R$_2$ and R$_3$ may be hydrogen, alkyl, aryl, heteroaryl, aralkyl or alkylaryl groups. Preferably R$_1$, R$_2$ and R$_3$ are hydrogen and/or alkyl groups having between 1 and about 10 carbon atoms. More preferably, R$_1$, R$_2$ and R$_3$ are hydrogen or methyl groups. Highly preferred examples of polyalkylene glycol compounds include diethylene glycol, dipropylene glycol, triethylene glycol, and tetraethylene glycol. Tetraethylene glycol is the most preferred polyalkylene glycol compound.

Alkylene glycol compounds provide at least a portion of the physical properties, solvency properties, polarity properties and hydrogen bonding properties that result in the desired selectivity and extractive solvent loading/capacity for separating mixtures of hydrocarbon compounds. Although alkylene glycols have a generally good thermal and chemical stability, they nevertheless undergo slow but significant thermal degradation over extended periods of time under the conditions typical of many extractive distillation processes.

The enhanced selectivity of the extractive distillation compositions of the invention are also related to the presence of at least one suitable compatibility agent. While not wishing to be bound by any theory, the compatibility agents of the invention are believed to function as materials which influence or improve the interaction and/or solubility between the alkylene glycol compounds (which are polar materials) and the mixture of hydrocarbons (which are often non-polar materials).

The one or more compatibility agents of the invention: are selected from materials having a polar parameter and a hydrogen bonding parameter such that the extractive distillation composition provides improved separation of the hydrocarbon compounds, as compared to the use of the extractive distillation composition without the compatibility agent. The improved separation of the hydrocarbon compounds is often reflected in greater selectivity of the separation, or higher purity, or higher capacity and/or loadings of the separated hydrocarbon compounds in the various product streams that result from extractive distillation processes which employ the compatibility agents.

The compatibility agents of the invention are preferably selected to have solvent solubility, dispersion, hydrogen bonding and/or polarity characteristics which are intermediate between the solvent solubility, dispersion, hydrogen bonding and/or polarity characteristics of the alkylene glycol (s), and the solvent solubility, dispersion, hydrogen bonding and/or polarity characteristics of the mixture of hydrocarbon derivatives.

Numerous attempts have been made to define, quantify, or otherwise characterize the solvent solubility, dispersion, hydrogen bonding, and/or polarity characteristics of various solvents and chemical compounds and compositions, by various methods and systems. Allen F. M. Barton {Chemical Reviews, 75(6), 731–753, (1975) ), and Handbook of Solubility Parameters and Other Cohesion Parameters, CRC Press, pg 94–110, and 153–161, (1983)} and H. Burrel {Polymer Handbook, 2nd Ed., J. Brandrup and E. H. Immergut, Ed, Interscience, New York City, section IV, pages 337–359 (1975)}, have described many of the various methods and systems of characterizing and quantifying solvent and/or solvency properties. The disclosure of these references regarding the methods and systems are hereby incorporated in their entireties by reference. Systems are known for the characterization of these physical characteristics by a single numerical Solubility Parameter (such as a Hildebrand Solubility Parameter), or with two Solubility Parameter components (such as polar and non-polar parameters). Such single parameter and double parameter systems are useful for selecting the compatibility agents of the instant invention.

Of even greater utility are three component or three parameter systems for characterizing the physical properties of solvents and chemical compounds. Three component or three parameter systems typically characterize chemical compounds by their dispersion, polar, and hydrogen bonding characteristics and/or parameters. The dispersion, polar, and hydrogen bonding characteristics and/or parameters of a wide array of known materials have been determined by various methods, based on a variety of types of experimental data and testing. Although it is impossible to measure such parameters for all the infinite number of possible chemical compounds, such parameters have been measured for hundreds or thousands of commonly available chemical compounds. The experimental determination of such characteristics and/or parameters require only routine and not excessive experimentation, which is within the average level of skill in the art.

In the methods provided by the instant invention, it has been found that superior compatibility agents can be selected by consideration of either i) previously known or ii) experimentally measured polar and/or hydrogen bonding characteristics and/or parameters of the candidate compounds or compositions. Suitable compatibility agents may be selected from materials having physical and/or solubility characteristics or parameters similar to those of the compatibility agents disclosed herein which provide improved separation of mixtures of hydrocarbon compounds in extractive distillation processes.

In many embodiments, the compatibility agent of the invention is a single chemical compound, selected on the basis of known or experimentally determinable Polar Parameters and Hydrogen Bonding Parameters. In other embodiments, the compatibility agent comprises a mixture of two or more materials wherein the mixture of two or more materials has a composite polar parameter and a composite hydrogen bonding parameter selected such that the extractive distillation composition provides improved separation of the hydrocarbon compounds. In yet other embodiments, the compatibility agent comprises a mixture of two or more materials, and each of the two or more materials has a polar parameter and a hydrogen bonding parameter selected such that the extractive distillation composition provides improved separation of the hydrocarbon compounds.

The particular solubility parameter system utilized to quantify the physical characteristics that determine the polar parameters and hydrogen bonding parameters of the potential compatibility agents is not critical to the practice of the invention. Nevertheless, one particularly well known and useful system for characterizing the "Polar Parameters" and "Hydrogen Bonding Parameters" of chemical compounds are "Hansen's Solubility Parameters." Hansen's Solubility Parameters take the general form $$\delta^2 = \delta^2_d = \delta^2_p = \delta^2_h$$

wherein $\delta$ is the Hildebrand single parameter;

$\delta_d$ is the Hansen's Solubility Dispersive or Non-polar Parameter $\delta_p$ is the Hansen's Solubility Polar Parameter; and $\delta_h$ is the Hansens's Solubility Hydrogen Bonding Parameter Hansen's Solubility Parameters can be expressed in various units, including $(Mpa)^{1/2}$ (Mpa=Megapascals), or $(calories/cm^3)^{1/2}$. The units used to express the Hansen's Solubility Parameters are not critical, so long as internal consistency is maintained. Unless otherwise stated, the units of the Hansen's Solubility Parameters stated in this application are $(calories/cm^3)^{1/2}$.

Protocols for experimentally determining the Hansen's Solubility Parameters of a given compound may be found in the references cited above, or the method described by Hansen (J. Paint Tech. 39, pg 505 (1967)), which are hereby incorporated by reference in their entireties. Hansen's Solubility Parameters have been determined for hundreds of common solvents and chemical compounds, as disclosed in the above-referenced articles by Barton and Burrel; by Barton in Handbook of Solubility Parameters and Other Cohesion Parameters, CRC Press pg 94–110, 153–161 (1983); by Technical Bulletin 1089–995, Jeffsol Carbonates, Comparative Solvents Data, published by Huntsman Corporation; and by Bulletin OP165–994-10M, Arcosolv Solvent Selector Chart, published by Lyondell Chemical; all of which are hereby incorporated by reference in their entireties, for their data on the solubility various chemical compounds, and teachings on various methods of determining solubility parameters.

Examples of known Hansen's Solubility Parameters for 26 common solvents are shown in Table 1 below and FIG. 1.

TABLE 1

HANSEN SOLUBILITY PARAMETERS-22 SOLVENT SET
(Units = $(calories/cm^3)^{1/2}$)

| | SOLVENT | $\delta_d$ | $\delta_p$ | $\delta_h$ |
|---|---|---|---|---|
| S-1 | Heptane | 7.5 | 0.0 | 0.0 |
| S-2 | Decaline | 8.8 | 0.0 | 0.0 |
| S-3 | Toluene | 8.8 | 0.7 | 1.0 |
| S-4 | Methylene Chloride | 8.9 | 3.1 | 3.0 |
| S-5 | Chlorobenzene | 9.3 | 2.1 | 1.0 |
| S-6 | Nitrobenzene | 9.8 | 4.2 | 2.0 |
| S-7 | Methanol | 7.4 | 6.0 | 10.9 |
| S-8 | Isopropanol | 7.7 | 3.0 | 8.0 |
| S-9 | n-Octanol | 8.3 | 1.6 | 5.8 |
| S-10 | Ethylene Glycol | 8.3 | 5.4 | 12.7 |
| S-11 | Dipropylene Glycol | 7.8 | 9.9 | 9.0 |
| S-12 | Tetrahydrofurfuryl Alcohol | 9.8 | 5.0 | 7.8 |
| S-13 | Dipropylene Glycol Dimethyl Ether | 7.4 | 3.0 | 6.3 |
| S-14 | Acetone | 7.6 | 5.1 | 3.4 |
| S-15 | Methyl Isobutyl Ketone | 7.5 | 3.0 | 2.0 |
| S-16 | Diacetone Alcohol | 7.7 | 4.0 | 5.3 |
| S-17 | Propylene Carbonate | 9.8 | 8.8 | 2.0 |
| S-18 | DBE ™ (Dibasic Esters from Dupont) | 8.3 | 2.3 | 4.8 |
| S-19 | Dimethylsulfoxide | 9.0 | 8.0 | 5.0 |
| S-20 | Acetonitrile | 7.5 | 8.8 | 3.0 |
| S-21 | N-methyl-pyrrolidone | 8.8 | 6.0 | 3.5 |
| S-22 | Dimethylformamide | 8.5 | 6.7 | 5.5 |
| | Gamma-butyrolactone | 9.3 | 8.1 | 3.6 |
| | N,N-dimethylacetamide | 8.2 | 5.6 | 5.0 |
| | Formamide | 8.4 | 12.8 | 9.3 |
| | Triethylene glycol | 7.8 | 6.1 | 9.1 |

As can be seen in Table 1, the Hansen's Dispersive Solubility Parameters ($\delta_d$) do not vary widely with the nature of the solvent/compound, but the Hansen's Polar Solubility Parameters ($\delta_p$), and Hansen's Hydrogen Bonding Parameters ($\delta_h$), vary significantly with the nature of the solvent/compound, as can also be seen in the Hansen Commercial Solvent Map Shown in FIG. 1. It is to be understood that in many embodiments of the invention, the Hansen's Polar Solubility Parameters ($\delta_p$), and Hansen's Hydrogen Bonding Parameters ($\delta_h$), of the mixture of hydrocarbon compounds will tend to be relatively small numbers. For example, heptane has Hansen's Solutility Parameters of $\delta_p=0.0$ and $\delta_h=0.0$, and toluene has Hansen's Solutility Parameters of $\delta_p=0.7$ and $\delta_h=1.0$. In many embodiments, the Hansen's Polar Solubility Parameters ($\delta_p$), and Hansen's Hydrogen Bonding Parameters ($\delta_h$), of the alkylene glycol compound will tend to be relatively high numbers, exemplified by those of triethylene glycol (i.e. $\delta_p=6.1$ and $\delta_h=9.1$).

In preferred embodiments of the invention, compatibility agents are selected from compounds that have the Hansen's Polar Solubility Parameters ($\delta_p$) and Hansen's Hydrogen Bonding Parameters ($\delta_h$), that are intermediate between the polar parameters and hydrogen bonding parameters of the one or more alkylene glycol compounds employed in the particular extractive distillation composition, and the polar parameters and hydrogen bonding parameters of the components of the particular mixture of hydrocarbon compounds that are to be separated by extractive distillation. It is to be understood that because particular mixtures of hydrocarbon compounds are to be separated, and a variety of alkylene glycols may be employed, the preferred ranges of polar parameters and hydrogen bonding parameters may vary with the identity of the hydrocarbon compounds and alkylene glycols.

In some embodiments of the invention, suitable compatibility agents are selected from chemical compounds or compositions which have a Hansen's Solubility Polar Parameter from about 2.7 to about 6.4 (calories/cm$^3$)$^{1/2}$, and a Hansen's Solubility Hydrogen Bonding Parameter from about 1.0 to about 4.4 (calories/cm$^3$)$^{1/2}$. In other embodiments of the invention, suitable compatibility agents have a Hansen's Solubility Polar Parameter from about 3.2 to about 5.9 (calories/cm$^3$)$^{1/2}$, and a Hansen's Solubility Hydrogen Bonding Parameter from about 1.5 to about 3.9 (calories/cm$^3$)$^{1/2}$.

In preferred embodiments of the invention, suitable compatibility agents are selected from chemical compounds or compositions which have a Hansen's Solubility Polar Parameter from about 1.0 to about 5.9 (calories/cm$^3$)$^{1/2}$, and a Hansen's Solubility Hydrogen Bonding Parameter from about 1.5 to about 5.9 (calories/cm$^3$)$^{1/2}$. In even more preferred embodiments of the invention, suitable compatibility agents are selected from chemical compounds or compositions which have a Hansen's Solubility Polar Parameter from about 1.3 to about 1.9 (calories/cm$^3$)$^{1/2}$, and a Hansen's Solubility Hydrogen Bonding Parameter from about 3.2 to about 5.8 (calories/cm$^3$)$^{1/2}$.

Additionally, the extractive distillation compositions of the invention, and/or compatibility agents contained therein preferably have a boiling point higher than the boiling point of the mixture of hydrocarbon compounds. A relatively high boiling point and/or relatively low volatility of the extractive distillation composition and/or compatibility agent slows or prevents their vaporization when employed in extractive distillation processes. Therefore, the compatibility agent tends to remain in the solution and/or liquid state, and flow downward toward the lower portion of an extractive distillation zone, while interacting with, and separating components of the mixture of hydrocarbon compounds within the distillation zone. Because the feed mixtures of hydrocarbon compounds which are subjected to extractive distillation typically have normal boiling points below 185° C., preferred compatibility agents for the compositions and processes of the invention have a normal boiling point exceeding 185° C. In more preferred embodiments of the invention, the compatibility agent has a normal boiling point from about 190° C. to about 400° C.

In preferred embodiments of the invention, the compatibility agent comprises at least one substituted or unsubstituted derivative of:

a. a dialkyl phthalate ester,
b. a cinnamate ester,
c. a C6–C12 alkyl ester of acetic, propionic, or butyric acid,
d. a C7–C10 methyl-alkyl ketone,
e. a dialkylester of succinic, glutaric, adipic or sebacic acids, or a mixture thereof,
f. a $C_8$–$C_{18}$ saturated or unsaturated acyclic alcohol,
g. a $C_4$–$C_{12}$ alkylene carbonate,
h. an alkoxypropyl or alkoxyisopropyl derivative of formamide or acetamide,
i. a methyl or ethyl ester of a $C_{10}$–$C_{18}$ carboxylic acid,
j. an amino-, nitro-, cyano-, acetyl-, and dichloro- derivative of benzene,
k. a polyalkylene glycol diester, or monoether ester.

Preferred substituent groups for the substituted derivative compatibility agents described above include but are not limited to alkyl groups, alkoxy groups, aromatic groups, heteroaromatic groups, alcohol groups, aldehyde groups, ketone groups, carboxylic acid or ester groups, thiol or thio-ether groups, amine groups, amide groups, and the like. Preferably the compatibility agents of the invention comprise at least one aromatic residue.

Preferably, the above-described mixture of a dialkylester of succinic, glutaric, and adipic acids comprises the mixture of Dibasic Esters which is produced by Dupont Corporation, or a substantially equivalent mixture of dicarboxylic acid esters.

In certain preferred embodiments of the invention, the compatibility agent comprises one or more of 2-ethyl-1-hexanol, dipropylene glycol methyl ether acetate, 1-octanol, 1-tridecanol, oleyl alcohol, 1-decanol (decyl alcohol), ethylene glycol dibutyrate, 1,2-decane carbonate, 1,2-dodecane carbonate, N-(2-aminoethyl)piperazine, aniline, 1,2-butylene carbonate, isobutyl heptyl ketone, dimethyl adipate, dimethyl glutarate, dimethylsuccinate, di-n-butyl sebacate, o-dichlorobenzene, diethyl succinate, diisobutylcarbinol, N,N-dimethylacetamide, ethylene glycol butyl ether, ethyl decanoate, 2-ethylhexyl acetate, a hexyl acetate, a heptyl acetate, an octyl acetate, a nonyl acetate, a decyl acetate, N-formyl morpholine, hexamethylphosphoramide, 1,2-hexane carbonate, 1-isopropyl-2-methyl imidazole, 3-isopropyl-2-oxazolidinone, methoxyisopropyl acetamide, methoxyisopropyl formamide, methoxypropyl acetamide, methoxypropy formamide, methyl oleate, nonylphenol, 2-octanol, propylene glycol diacetate, pine oil, iso-propyl palmitate, alpha-terpineol, tri-n-butyl phosphate, acetophenone, benzonitrile, di-n-butyl phthalate, diethyl phthalate, dimethyl phthalate, ethyl cinnamate, isophorone, nitrobenzene, or quinoline.

In other preferred embodiments of the invention, the compatibility agent comprises 2-ethyl-1-hexanol, dipropylene glycol methyl ether acetate, 1-octanol, 1-tridecanol, oleyl alcohol, 1-decanol (decyl alcohol), ethylene glycol dibutyrate, 1,2-decane carbonate, 1,2-dodecane carbonate.

In some embodiments of the invention, the compatibility agent does not comprise an N-hydrocarbyl substituted-2-thiopyrrolidone residue or compound. In other embodiments of the invention, the compatibility agent does not comprise an N-hydrocarbyl substituted-pyrrolidone residue or compound. The hydrocarbyl substituent groups of the N-substituted-2-thiopyrrolidone and/or N-substituted-pyrrolidone residues or compounds may include hydrogen, alkyl, alkylene, or aromatic groups, which may or may not be further substituted with groups such as hydroxy groups, alkoxy groups, amine groups, thiol groups, and the like.

In other embodiments of the present invention, the compatibility agent is not a polyalkyleneglycol ether compound of the formula:

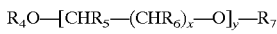

wherein $R_4$, $R_5$, $R_6$ and $R_7$ may be hydrogen alkyl, aryl, aralkyl, alkylaryl and mixtures thereof, and wherein $R_4$ or $R_7$ are not both hydrogen. Preferably, the compatibility agent does not comprise a monoalkyl ether of ethylene glycol, propylene glycol, or 1,4-butanediol, the monomethyl ether or triethylene glycol, or a monoalkyl ether of a polyether compounds derived from ethylene glycol, propylene glycol, 1,4-butanediol, or their residues, or mixtures thereof.

Preferably, the compatibility agent comprises a minor amount of the extractive distillation composition. More preferably, the compatibility agent comprises from about 1 to about 50 parts by weight of the extractive distillation composition per 100 parts alkylene glycol. More preferably, the compatibility agent comprises from about 5 to about 35 parts by weight of the extractive distillation composition per 100 parts alkylene glycol. Most preferably, the compatibility agent comprises from about 15 to about 25 parts by weight of the extractive distillation composition per 100 parts alkylene glycol.

In certain embodiments, the extractive distillation composition comprises at least one dialkyl sulfone having three to nine carbon atoms. Examples of such dialkyl sulfone compounds include methyl ethyl sulfone, methyl propyl sulfone, ethyl propyl sulfone, di-n-propyl sulfone, di-isobutyl sulfone, and the like.

A preferred dialkyl sulfone is dimethyl sulfone i.e. $CH_3$—$SO_2$—$CH_3$ (often abbreviated "$DMSO_2$" or "MSM" (an abbreviation for methyl sulfonyl methane). $DMSO_2$ is a high boiling, thermally stable material that is readily commercially available and relatively inexpensive. Moreover, $DMSO_2$ has solvency properties and extractive distillation behavior that is similar to that of alkylene glycols, but because of its very high thermal stability, $DMSO_2$ extends the recycle life of the extractive distillation composition, by effectively substituting for alkylene glycols, which have a lower thermal stability than $DMSO_2$. This substitution allows the extractive distillation composition to be reused and recycled to a greater extent, minimizing make-up of the extractive distillation composition, and the associated expenditures.

In preferred embodiments, the dialkylsulfone or the dimethyl sulfone is present in an amount effective to provide the extractive distillation composition with improved thermal stability as compared to the extractive distillation composition which does not include the dimethyl sulfone. Preferably, the extractive distillation composition comprises from about 0.1 parts to about 50 parts by weight of dimethylsulfone, per 100 parts of alkylene glycol. More preferably, the extractive distillation composition comprises from about 10 parts to about 35 parts by weight of dimethylsulfone. Even more preferably, the extractive distillation composition comprises from about 15 parts to about 30 parts by weight of dimethylsulfone. A composition which is 36% dimethyl sulfone and 36% tetraethylene glycol by weight is an alternative preferred embodiment. A composition which is 50% dimethyl sulfone and 50% tetraethylene glycol by weight is another alternative preferred embodiment.

In some preferred embodiments, the extractive distillation composition further comprises water. Minor amounts of water may improve the selectivity of extractive distillation compositions for separation of the hydrocarbon compounds, lower the boiling point of the extractive distillation composition, and/or improve miscibility of the components of the extractive distillation composition. Preferred embodiments of the extractive distillation composition of the invention may further comprise from about 0.1 parts to about 10 parts water per 100 parts of alkylene glycol. More preferably, the extractive distillation composition further comprises from about 2 parts to about 5 parts water per 100 parts of alkylene glycol. The extractive distillation composition may also advantageously comprise conventional surfactants, corrosion inhibitors, or antioxidants.

The above described extractive distillation compositions of the invention can be employed in a process for separating a mixture of hydrocarbon compounds by extractive distillation. The extractive distillation processes of this invention are not necessarily limited to any particular set of steps, apparatus, and/or operating procedures, as many variations of such steps, apparatus, and/or procedures are known to those of skill in the art, and are disclosed, inter alia, in the above-referenced patents.

Nevertheless, in a preferred embodiment, the invention provides a process for separating hydrocarbon compounds of similar boiling points by extractive distillation, comprising the steps of:

a. contacting a feed mixture with an extractive distillation composition within an extractive distillation zone, wherein the feed mixture comprises at least
  i. a first hydrocarbon compound, and
  ii. a second hydrocarbon compound; and
b. distilling the feed mixture to at least partially separate the feed mixture into a first stream enriched in the first hydrocarbon compound, and a second stream enriched in the second hydrocarbon compound; and wherein the extractive distillation composition comprises
  i. at least one alkylene glycol compound, and
  ii. at least one compatibility agent, wherein the at least one compatibility agent is selected from materials
    (1) having a polar parameter and a hydrogen bonding parameter such that the extractive distillation composition provides improved separation of the hydrocarbon compounds, as compared to the use of the extractive distillation composition without the compatibility agent; and
    (2) having a boiling point higher than the boiling point of the mixture of hydrocarbon compounds;

In many embodiments of the processes of the invention, the feed mixture is introduced into an extractive distillation zone, which often has an upper portion and a lower portion. The extractive distillation zones suitable for the invention can comprise a wide variety of equipment and devices suitable for distillation processes, such as tanks, vessels, pipes, tubing, heat exchangers, reboilers, wiped film or falling film evaporators, distillation columns, and the like. The extractive distillation zones are often provided with means for ensuring intimate physical contact between the feed mixtures and the extractive distillation composition during the extractive distillation process, such as trays, packing materials, condensers, and the like. The extractive distillation zones often comprise distillation columns, the design and operation of which are well known to those of skill in the art. The distillation columns may be packed with various materials which provide high surface areas, and/or ensure a tortuous path for inducing mixing of gases and liquids. The distillation columns may also have trays, which collect liquid and have means for inducing the interaction of the liquid with vapors within the column.

Many embodiments of the extractive distillation processes of the invention comprise introducing the extractive distillation composition into the upper portion of the extractive distillation zone, so that it may flow downward as the distillation occurs, and intimately intermix with the feed mixture. The feed mixture is preferably introduced into a lower portion of the extractive distillation zone, so that the more volatile components vaporize and flow upward in the distillation zone. Preferably, the extractive distillation composition is not introduced at the uppermost portion of the extractive distillation zone, so as to ensure that it does not contaminate the overhead stream, which is typically enriched in the more volatile and/or less polar components of the feed mixture, such as the first hydrocarbon compound. In a preferred embodiment, the extractive distillation process further comprises withdrawing the overhead stream from the upper portion of the extractive distillation zone. The pressure in the extractive distillation zone may be subatmospheric, approximately atmospheric, or superatmospheric. Preferably, the pressure in extractive distillation zone is from about 1 atmosphere to about 5 atmospheres.

The feed mixtures utilized in the extractive distillation processes can include complex mixtures of wide varieties of chemical compounds and/or hydrocarbons. Typically, the compounds comprise mixtures of hydrocarbon compounds and/or petroleum distillates, which may be unsubstituted, or substituted with a wide variety of alkyl groups, alkylene groups, aromatic groups, heteroatoms (including oxygen, nitrogen, silicon, sulfur, phosphorus or halogens), or heteroatomic groups or residues which contain heteroatoms. The hydrocarbon compounds may be branched or unbranched, saturated or unsaturated, cyclic or heterocyclic, aromatic, or substituted aromatic compounds.

In preferred embodiments, the feed mixture comprises a first hydrocarbon compound of relatively low polarity and/or hydrogen bonding capacity, and a second hydrocarbon compound having relatively higher polarity and/or hydrogen bonding capacity. For example, the feed mixture may comprise isomers with differing polarities, such as para-xylene and ortho-xylene. Preferably, the first hydrocarbon compound comprises at least one saturated hydrocarbon residue (exemplified by alkyl groups such as methyl, ethyl, or higher alkyl groups), and a second hydrocarbon compound comprising at least one carbon-carbon double bond (such as mono-olefins, polyolefins, and/or aromatics).

In many embodiments, the extractive distillation process at least partially separates the feed mixture into a first stream enriched in the first hydrocarbon compound, and a second stream enriched in the second hydrocarbon compound. Often, the first hydrocarbon compound is relatively nonpolar as compared to the second hydrocarbon compound. While not wishing to be bound by theory, it is believed that the second hydrocarbon typically interacts significantly with the extractive distillation composition, and therefore combines with the extractive distillation composition, to produce the second stream. In many embodiments, the second stream exits the extractive distillation zone from a lower portion of the distillation zone, to form a "bottoms" stream. The bottoms steam preferably comprises a mixture of the extractive distillation composition and the second hydrocarbon compound. Preferably, the bottoms stream is relatively enriched in the second hydrocarbon compound and relatively depleted in the first hydrocarbon compound, as compared with the feed mixture.

In contrast to the second hydrocarbon compound, the typically less polar first hydrocarbon compound often interacts less strongly with the extractive distillation composition. As a result, the volatility of the first hydrocarbon compound is not greatly depressed, so that it preferentially vaporizes, and its concentration is enhanced in the first stream, that typically exits the extractive distillation zone from an upper portion of the extractive distillation zone, to form an "overhead" stream.

In one embodiment, the extractive distillation process further comprises withdrawing the second stream from the lower portion of the extractive distillation zone. In another preferred embodiment, the extractive distillation process further comprises treating the bottoms stream to separate the second hydrocarbon compound from the extractive distillation composition. The treatment that separates the second hydrocarbon compound from the extractive distillation composition often comprises an additional distillation or extraction process.

In certain embodiments, wherein the extractive distillation composition comprises a compatibility agent and/or dimethyl sulfone, the second steam often acquires an improved capacity for selectively removing the second hydrocarbon compound from the feed material, as gauged by the absolute quantity or mass of the second hydrocarbon compound separated. Viewed in a different way, in the presence of the compatibility agent and/or dimethyl sulfone, the loading of the second hydrocarbon compound in the second stream (as gauged by weight or mole percentage, or other similar measures) increases. Therefore, in embodiments employing the compatibility agents and/or dimethyl sulfone, the bottoms stream may have a higher loading of the second hydrocarbon compound than the loading of the second hydrocarbon compound obtained in the absence of the compatibility agent and/or dimethyl sulfone. High loadings of the second hydrocarbon compound in the second streams are particularly desirable when the second hydrocarbon compound comprises a valuable aromatic compound, or a mixture of aromatic compounds, such as benzene, toluene, xylenes, or mixtures thereof.

In a preferred embodiment, the feed mixture comprises a mixture of aliphatic and olefinic compounds, wherein the first hydrocarbon compound is an aliphatic compound or mixture of aliphatic compounds, and the second hydrocarbon compound is an olefinic compound or a mixture of olefinic compounds. In another preferred embodiment, the first hydrocarbon compound comprises at least one saturated hydrocarbon residue, and the second hydrocarbon compound comprises at least one carbon-carbon double bond.

In certain embodiments, the first hydrocarbon compound is a $C_7$–$C_{10}$ aliphatic compound. In other embodiments, the saturated hydrocarbon residue of the first hydrocarbon compound comprises at least two carbon atoms.

In many embodiments, the second hydrocarbon compound comprises an aromatic residue. In more preferred embodiments, the second hydrocarbon compound is a $C_6$–$C_{10}$ substituted benzene compound. In certain highly preferred embodiments, the second hydrocarbon compound is benzene, toluene, ortho-xylene, meta-xylene, para-xylene, or a mixture thereof.

In many preferred embodiments of the invention, the feed mixture comprises a mixture of aliphatic, olefinic, and/or aromatic compounds. Such mixtures are common in the hydrocabon and oil refining industries, and are often produced in pyrolysis gasoline units, or catalytic reforming units. In one highly preferred embodiment, the feed mixture comprises a BTX stream. BTX streams are very common in petroleum and hydrocarbon refining and recovery processes, and comprise mixtures of benzene, toluene, para-xylene, meta-xylene, ortho-xylene, in mixtures also comprising other saturated hydrocarbons or olefins having normal boiling points similar to those of benzene, toluene, para-xylene, meta-xylene and ortho-xylene. The saturated hydrocarbons of BTX streams typically comprise mixtures of isomeric C6–C10 alkanes and/or olefins. In refinery operations, the aromatic compounds generally are of higher value, and the objective of extractive distillation of BTX streams is to selectively purify and/or recover the aromatics from mixtures. A selective extractive distillation solvent often enhances the concentration of aliphatic/non-aromatic materials in the extractive distillate (raffinate, in refinery parlance) relative to that of the aromatic components.

In another preferred embodiment, the feed mixture comprises ethylbenzene, styrene, or a mixture thereof.

Although extractive distillation is often applied to separate a wide variety of mixtures of hydrocarbon compounds, including very complex multi-component mixtures, or azeotropic mixtures (which form in either the presence or absence of water), extractive distillation is often employed when certain components of the hydrocarbon mixture have similar normal boiling points or volatilities. In preferred embodiments of the processes of the invention, the first and second hydrocarbon compounds have normal boiling points that differ by less than 5° C. More preferably, the first and second hydrocarbon compounds have normal boiling points that differ by less than 2° C.

One highly preferred embodiment of the invention provides a process for separating hydrocarbon compounds of similar boiling points by extractive distillation, comprising the steps of:

a. introducing a feed mixture into an extractive distillation zone having an upper portion and a lower portion, wherein the feed mixture comprises at least
   i. a first hydrocarbon compound comprising a $C_7$–$C_{10}$ aliphatic compound, and
   ii. a second hydrocarbon compound comprising benzene, toluene, ortho-xylene, meta-xylene, para-xylene, or a mixture thereof; and b. introducing an extractive distillation composition into the upper portion of the extractive distillation zone; and c. distilling the feed mixture to at least partially separate the feed mixture into a first stream rich in the first hydrocarbon compound, and a second stream rich in the second hydrocarbon compound; wherein the extractive distillation composition comprises:
   i. about 100 parts by weight of at least one alkylene glycol, and
   ii. from about 5 to about 35 parts by weight of a compatibility agent or a mixture of compatibility agents, wherein the compatibility agent comprises 2-ethyl-1-hexanol, dipropylene glycol methyl ether acetate, 1-octanol, 1-tridecanol, oleyl alcohol, 1-decanol (decyl alcohol), ethylene glycol dibutyrate, 1,2-decane carbonate, 1,2-dodecane carbonate, N-(2-aminoethyl)piperazine, aniline, 1,2-butylene carbonate, isobutyl heptyl ketone, dimethyl adipate, dimethyl glutarate, dimethylsuccinate, di-n-butyl sebacate, o-dichlorobenzene, diethyl succinate, diisobutylcarbinol, N,N-dimethylacetamide, ethylene glycol butyl ether, ethyl decanoate, 2-ethylhexyl acetate, a hexyl acetate, a heptyl acetate, an octyl acetate, a nonyl acetate, a decyl acetate, N-formyl morpholine, hexamethylphosphoramide, 1,2-hexane carbonate, 1-isopropyl-2-methyl imidazole, 3-isopropyl-2-oxazolidinone, methoxyisopropyl acetamide, methoxyisopropyl formamide, methoxypropyl acetamide, methoxypropy formamide, methyl oleate, nonylphenol, 2-octanol, propylene glycol diacetate, pine oil, iso-propyl palmitate, alpha-terpineol, tri-n-butyl phosphate, acetophenone, benzonitrile, di-n-butyl phthalate, diethyl phthalate, dimethyl phthalate, ethyl cinnamate, isophorone, nitrobenzene, or quinoline.

In yet a different aspect, the invention relates to a process for separating a mixture of hydrocarbon compounds by extractive distillation that employs an extractive distillation composition, wherein the improvement comprises the use of a mixture comprising at least one alkylene glycol compound, and at least one compatibility agent, wherein the at least one compatibility agent:

a. is selected from materials having a polar parameter and a hydrogen bonding parameter such that the extractive distillation composition provides improved separation of the hydrocarbon compounds, as compared to the use of the extractive distillation composition without the compatibility agent; and b. has a boiling point higher than the boiling point of the mixture of hydrocarbon compounds.

In alternative aspects, the invention provides the products produced by the extractive distillation processes of the invention. The products of the processes of the invention preferably comprise, the first stream, the second stream, the high purity hydrocarbon compounds produced by further treatment of the first or second streams, and the extractive distillation composition recovered from the extractive distillation zone. In many embodiments, any extractive distillation composition so recovered is recycled to an extractive distillation zone.

The extractive distillation compositions and extractive distillation processes of the invention often have the advantage of ready implementation in existing alkylene glycol-based aromatic extraction units, which are common in the refineries and manufacturing facilities of the chemical and hydrocarbon industries. The improvements and advantages (such as increased product capacity and lower utility and energy costs) are often obtained at relatively low capital cost. The raw material requirements of the process of this invention also compare favorably with that of conventional alkylene glycol-based processes, and can offer improved extractive solvent loading, enhanced extraction selectivity, and higher thermally stability and longer recycle life than the extractive distillation solvents currently in use in the hydrocarbon industry.

Experimental

The following examples are put forth so as to provide those of ordinary skill in the art with a complete disclosure and description of how the compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.) But some errors and deviations should be accounted for. Unless indicated otherwise, parts are parts by weight, temperature is in ° C. or is at ambient temperature, and pressure is at or near atmospheric.

Protocol for Extractive Distillation Selectivity Experiments

A hydrocarbon mixture containing 0.5 parts by weight of toluene and 0.5 parts of n-heptane, was combined with four parts by weight of an extractive distillation composition (of a specified composition comprising tetraethylene glycol, compatibility agent, dimethylsulfone, and/or water), and placed in a distillation apparatus designed to vaporize, then condense and collect an overhead extractive distillate phase. The volume of the mixture was held essentially constant between experiments, to eliminate differences attributable to heating and distillation effects in the apparatus. The mixture was then heated to its boiling point, and a measured volume of the extractive distillate phase (hydrocarbon raffinate) was collected, and analyzed using gas chromatography for heptane and toluene. Selectivity is quantified in the cited examples as the weight % heptane in the extractive distillate phase.

Experiments without compatibility agent (i.e. control experiments) were also performed, and the results compared to experiments which used a compatibility agent.

EXAMPLE 1

Isophorone Compatibilized TEG-DMSO2 Experiment

Figure 2:
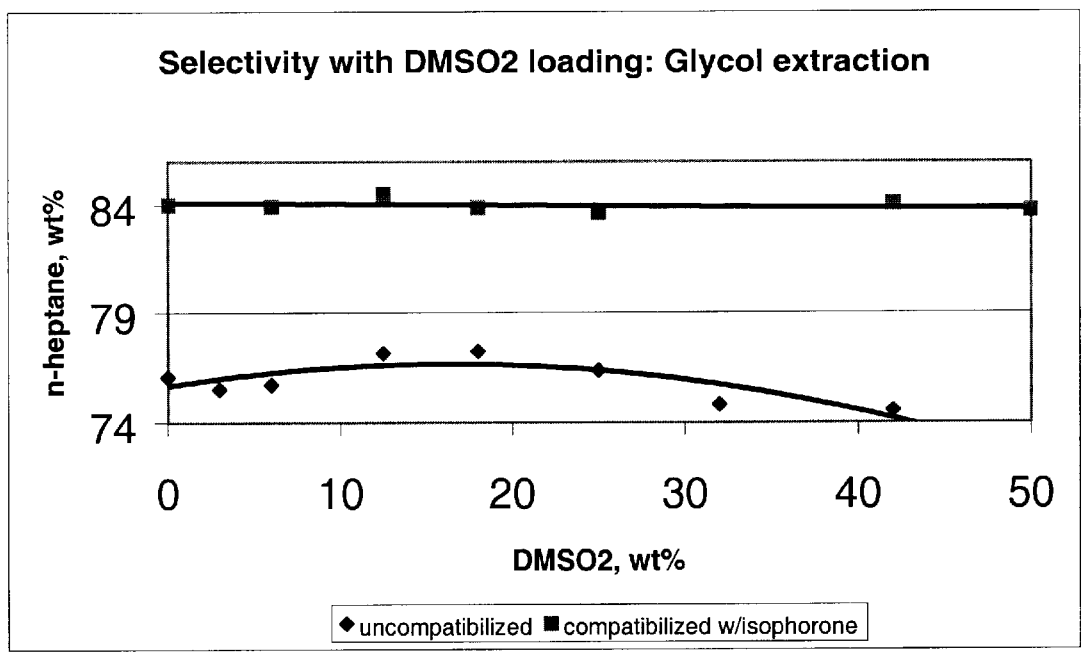
FIG. 2 shows the results of selectivity experiments for mixtures of n-heptane and toluene, with and without isophorone compatibility agent, as a function of the weight % of dimethylsulfone in tetraethylene glycol.

In an experiment typical of the series of experiments summarized in Table 2 and FIG. 2, an extractive distillation composition was prepared by mixing 27.8 g tetraethylene glycol, 20.16 g dimethyl sulfone (i.e., 58% tetraethylene glycol, 42% dimethylsulfone), 2.4 g H2O and 16.5 g of isophorone compatibility agent were mixed, to give a total of 66.9 grams of the extractive distillation composition, which was added to the experimental distillation apparatus. A feed mixture of 12.0 g of a mixture of 6.0 g toluene and 6.0 g n-heptane was also added to the distillation apparatus. The resulting mixture was carefully distilled and the first 2.0 mL overhead distillate was collected. The resulting extractive distillate analyzed at 84.1% n-heptane (see Table 2, row 8, column 3).

EXAMPLE 2

Uncompatibilized TEG-DMSO2 Experiment

In a comparative experiment, (which did not employ the isophorone compatibility agent) 22.8 g dimethyl sulfone, 34.2 g tetraethylene glycol (i.e., 58% tetraethylene glycol, 42% dimethylsulfone), and 3.0 g H2O were mixed to give 60.0 grams of extractive distillation composition. The feed mixture comprised comprised of 7.5 g toluene and 7.5 grams n-heptane. The resulting mixture was again carefully distilled, collecting the first 2.0 mL of the extractive distillate. The resulting extractive distillate analyzed at 74.59% n-heptane (see Table 2, row 8, column 2).

Similar experiments were conducted utilizing extractive distillation compositions having lower percentages of dimethyl sulfone, (and correspondingly higher percentages of tetraethylene glycol (See Table 2, rows 2–7, and FIG. 2).

TABLE 2

Selectivity with DMSO2 loading (with and without Isophorone Compatibilizer).

| DMSO$_2$ (wt %) | Uncompatibilized result (wt % heptane) | Compatibilized w/isophorone result (wt % heptane) |
|---|---|---|
| 0 | 76.062 | 84.028 |
| 3 | 75.538 | |
| 6 | 75.728 | 83.954 |
| 12.5 | 77.157 | 84.542 |
| 18 | 77.239 | 83.899 |
| 25 | 76.360 | 83.671 |
| 32 | 74.838 | |

TABLE 2-continued

Selectivity with DMSO2 loading (with and without Isophorone Compatibilizer).

| DMSO$_2$ (wt %) | Uncompatibilized result (wt % heptane) | Compatibilized w/isophorone result (wt % heptane) |
|---|---|---|
| 42 | 74.586 | 84.1 |
| 50 | | 83.77 |

As can be seen in FIG. 2, the extractive distillation composition compatibilized with isophorone (denoted in FIG. 2 as "compatibilized") is markedly more selective than the uncompatibilized formulation, (denoted "uncompatibilized") over the entire range of dimethylsulfone compositions. This phenonenon was observed throughout the range of dimethylsulfone compositions investigated. Thus, an enhancement in selectivity of 7–10% is achieved at all dimethyl sulfone loadings. This improvement is considerable in view of the fact that modest selectivity enhancements may result in substantial economic gains in BTX operations.

EXAMPLE 3

Acetophenone Compatibilized TEG-DMSO2 Experiment

Figure 3:
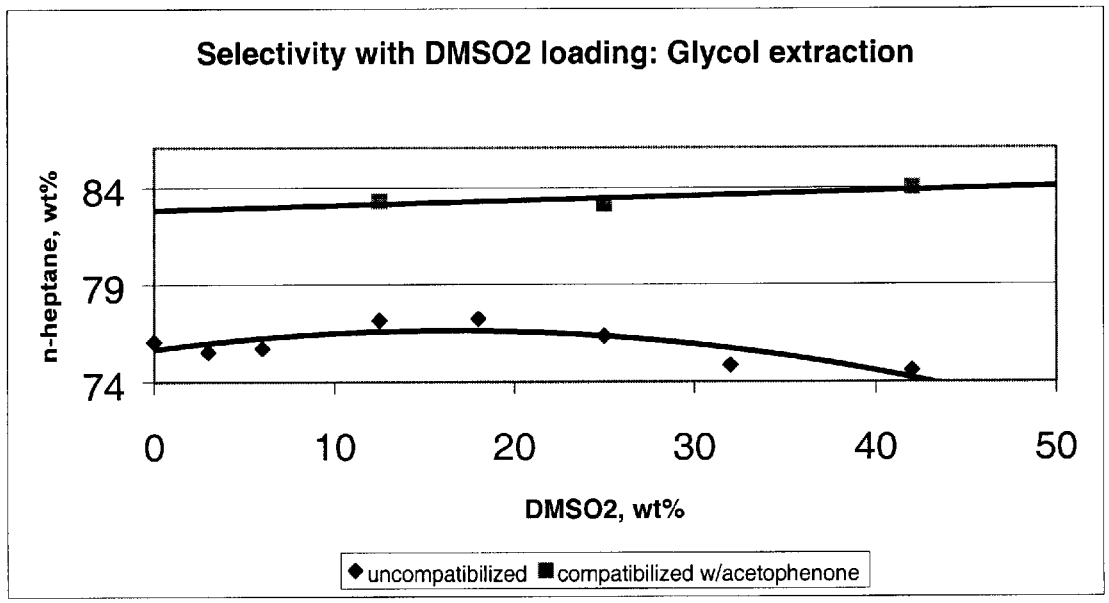
FIG. 3 shows the results of selectivity experiments for mixtures of n-heptane and toluene, with and without acetophenone compatibility agent, as a function of the weight % of dimethylsulfone in tetraethylene glycol

An extractive distillation composition was prepared by mixing 27.8 grams of tetraethylene glycol, 20.1 grams of dimethyl sulfone (i.e. 58% tetraethylene glycol and 42% dimethyl sulfone), 2.4 grams H2O, and 16.5 grams of acetophenone as a compatibility agent. The extractive distillation composition was charged to an experimental distillation apparatus, along with a feed mixture of 6.0 grams of toluene and 6.0 grams of n-heptane. The resulting mixture was carefully distilled and the first 2.0 mL of overhead distillate was collected. The resulting extractive distillate analyzed at 84.0% n-heptane. Other similar experiments were conducted using acetophenone as a compatibility agent, and are shown in Table 3 and FIG. 3 above.

EXAMPLE 4

Relative Thermal Stabilities of TEG and DMSO2 at 140° C.

The relative thermal stabilities of tetraethylene glycol and dimethyl sulfone were compared. Samples of dimethyl sulfone and tetraethylene glycol (10.0 g) were placed in 50-ml screw-top vials and placed in an oil bath maintained at 140° C. Commercial samples of dimethyl sulfone and tetraethylene glycol were guaranteed at 99% purity. Aliquots of the heated sample were analyzed at 0, 24, 48, and 96 hours by gas chromatography, and the formation of impurities was monitored with time. The results are shown in Table 4, and FIG. 4.

TABLE 4

Relative Thermal Stabilities of TEG and DMSO2 at 140° C.

| Time (hr.) | wt % impurities) - TEG | wt % impurities) - DMSO2 |
|---|---|---|
| 0 | 0.35 | 0.056 |
| 24 | 1.69 | 0.055 |
| 48 | 3.30 | 0.046 |
| 96 | 4.80 | 0.061 |

Figure 4:
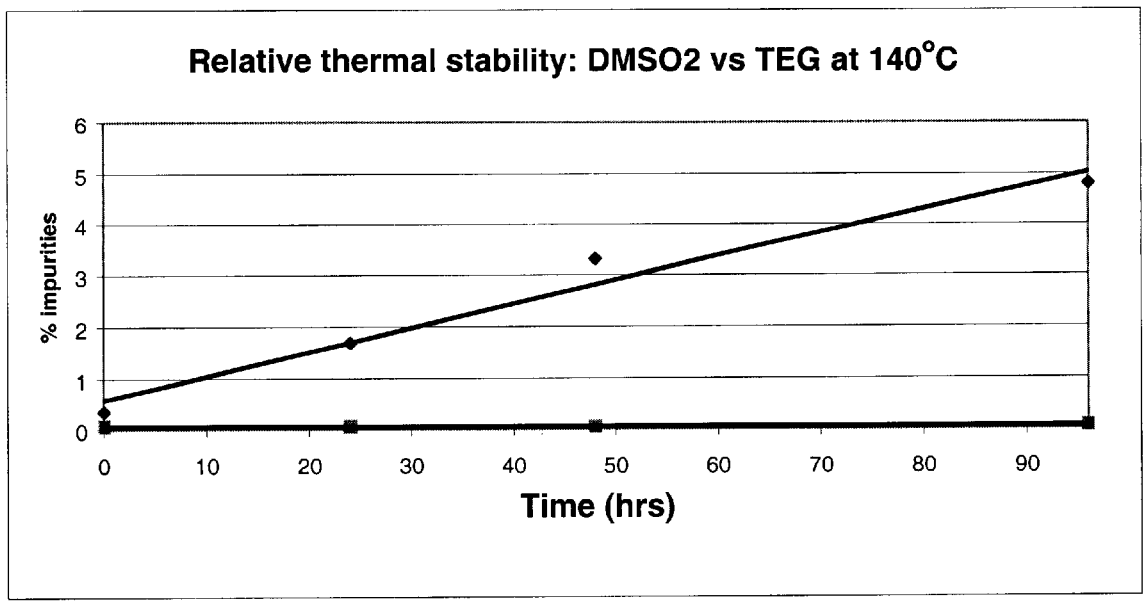
FIG. 4 shows the relative rates of thermal degradation of tetraethylene glycol and dimethyl sulfone ("$DMSO_2$") as a function of time.

As evidenced from the data in Table 4 and FIG. 4, dimethyl sulfone is more thermally stable than tetraethylene glycol. Over a 96 hr period, only a negligible quantity of impurities were generated in the dimethyl sulfone sample (0.005%). In contrast, the tetraethylene glycol sample became quite dark and 4.45% impurities developed. While this is seemingly a small value, this decomposition becomes problematic (and expensive) when extrapolated to a year's time. Thus, it might be expected that approximately 406.1% of the tetraethylene glycol would decompose after 365 days under these conditions. This should result in a considerable decrease in the need for makeup tetraethylene glycol. Therefore, due to its negligible decomposition at this temperature, 50% dimethyl sulfone loading in tetraethylene glycol extractive distillation units would be expected to reduce solvent decomposition to about half that currently observed.

Experimental Protocol for Loading Experiments

"Loading" is a measure of the amount of the aromatic compounds contained in the extractive distillation composition produced by an extractive distillation.

The apparatus and procedure used in the selectivity experiments above (Examples 1–3) were adapted for hydrocarbon loading experiments as follows. A hydrocarbon mixture containing 0.5 parts by weight of toluene and 0.5 parts of n-heptane were added to the above-described extractive distillation apparatus, along with three parts by weight of an extractive distillation composition of a specified composition (comprising tetraethylene glycol, dimethyl sulfone, compatibility agent, and/or water). The weight of the resulting mixture was held constant at 56.0±2 g between experiments.

The mixture was then heated to its boiling point, and a measured volume (2.0 ml) of the extractive distillate phase distilled overhead (hydrocarbon raffinate) was collected and analyzed using gas chromatography, for heptane and toluene. The weight and volume of the liquid mixture remaining in the lower portion of the extractive distillation apparatus was measured by pouring the hot mixture into a heated, tared measuring cylinder, and weighing on an analytical balance. In most experiments, the mixture was a two phase mixture, comprising an extractive solvent phase (bottom phase) and a hydrocarbon feed phase (top phase). After removing the hydrocarbon feed phase by pipette, the weight of the remaining extractive phase was determined. The weight of the hydrocarbon feed phase removed by pipette was calculated by difference. Aliquots of both top and bottom phases were diluted in a weighed amount of methylene chloride and analyzed using gas chromatography for heptane and toluene. A mass balance for the system was calculated, and found in good agreement with the total initial charge (see Table 5, column 4, row 1–4.

Changes in aromatics loading or capacity were determined by GC analysis, and reported as the change in weight % toluene in the extractive solvent phase, relative to a reference experiment containing unmodified solvent. Thus, per cent loading may be defined as follows:

% Loading=((wt toluene$_{expt}$−wt toluene$_{ref}$)/wt toluene$_{ref}$)×100

EXAMPLE 5

Uncompatibilized TEG Loading Experiment

A reference experiment which contained no compatibilizer was carried out, as follows. An extractive distillation composition was prepared by mixing 56.31 g tetraethylene glycol (see Table 5, row 1, column 1–5) and 1.44 g H2O.

The total weight of the extractive distillation composition was 57.7 g. A feed mixture of 9.62 g toluene and 9.62 g n-heptane was added. The resulting mixture was carefully distilled and the first 2.0 mL overhead distillate collected and weighed. The weights and toluene content of the extractive solvent phase and the hydrocarbon feed phase were determined. Mass balance calculations showed that 96.7% of the initial charge was accounted for, and that the extractive solvent phase contained 4.48 g of toluene.

EXAMPLE 6

Isophorone compatibilized TEG Loading Experiment

In an experiment typical of the series of experiments summarized in Table 5, an extractive distillation composition was prepared by mixing 47.6 tetraethylene glycol, 1.44 g H2O and 8.4 g of isophorone compatibility agent. The total weight of the extractive distillation composition was 57.4 g, and the isophorone, comprised 15.0 weight % of the extractive solvent phase (see Table 5, row 3, column 1). A feed mixture of 9.62 g toluene and 9.62 g n-heptane was added. The resulting mixture was carefully distilled and the first 2.0 mL overhead distillate was collected and weighed. The weights of the extractive solvent phase, and the hydrocarbon feed phase were determined, and. mass balance calculations accounted for 97.75% of the initial charge. GC analysis of the extractive solvent phase showed 5.60 g of contained toluene (see Table 5, column 2, row 3). This result corresponds to an enhancement in aromatics loading or capacity in the extractive solvent phase of 1.12 g (25.0%), relative to the reference experiment (see Table 5, column 3, row 3).

Figure 5:
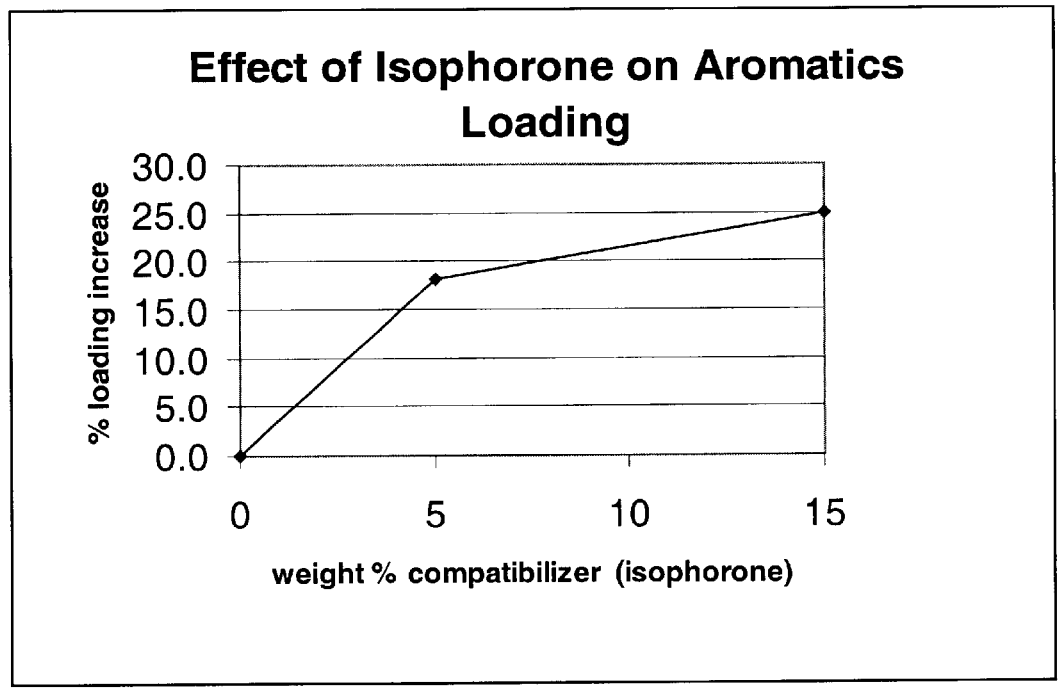
FIG. 5 shows the effect of isophorone concentration on aromatics loading.

It was observed that the weight of the extractive solvent phase was essentially constant over isophorone compatibilizer concentrations from 0–15%. Thus the observed increase in aromatics loading of the extractive solvent phase depended primarily on changes in the solvency characteristics of the extractive distillation composition. By contrast single phasing (complete compatiblization) was observed at 30% isophorone concentration, along with at a dramatic increase in aromatics loading in the resulting single phase, as a consequence of the single-phasing. The "single phasing" data point was omitted from FIG. 5, which represents loading enhancements in two phase systems. The two phase scenarios are preferably applicable to BTX extraction processes that employ unit operations involving an initial counter-current liquid-liquid extraction, and subsequent extractive distillation. The single phase scenarios are preferably applicable to processes which depend primarily or solely on extractive distillation to achieve separation of the BTX stream from the hydrocarbon raffinate phase. Thus, the extractive distillation compositions of the present invention afford an unexpected and desirable marriage of extraction performance, i.e. selectivity/loading advantages, with process flexibility.

TABLE 5

Effect of Isophorone Concentration on Aromatics Loading.

| weight % Isophorone | weight, g toluene (solvent) | change in loading % | mass balance | Weight, g Solvent phase |
| --- | --- | --- | --- | --- |
| 0 | 4.48 | 0.0 | 96.70 | 61.44 |
| 5 | 5.29 | 18.1 | 96.70 | 62.24 |
| 15 | 5.60 | 25.0 | 97.75 | 61.83 |
| 30 | 9.92 | 121.4* | 98.60 | 76.01* |

Throughout this application, various publications are referenced. The disclosures of these publications in their entireties are hereby incorporated by reference into this application for all purposes.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A process for separating hydrocarbon compounds of similar boiling points by extractive distillation, comprising the steps of:
   a. contacting a feed mixture with an extractive distillation composition within an extractive distillation zone, wherein the feed mixture comprises at least
      i. a first hydrocarbon compound, and
      ii. a second hydrocarbon compound; and
   b. distilling the feed mixture to at least partially separate the feed mixture into a first stream enriched in the first hydrocarbon compound, and a second stream enriched in the second hydrocarbon compound; and wherein the extractive distillation composition comprises,
      i. at least one akylene glycol compound, and
      ii. at least one compatibility agent, wherein the at least one compatibility agent is selected from materials
         (1) having a Hansen's Solubility Polar Parameter from about 2.7 to about 6.4 (calories/cm$^3$)$^{1/2}$, and a Hansen's Solubility Hydrogen Bonding Parameter from about 1.0 to about 4.4 (calories/cm$^3$)$^{1/2}$;
         (2) having a boiling point higher than the boiling point of the mixture of hydrocarbon compounds; and
         (3) does not comprise
            (a) an N-hydrocarbyl-substituted pyrrolidone compound or residue, or an N-hydrocarbyl-substituted-2-thiopyrrolidone compound or residue, or
            (b) a polyalkyleneglycol ether compound of the formula:

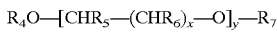

wherein $R_4$, $R_5$, $R_6$ and $R_7$ may be hydrogen alkyl, aryl, aralkyl, alkylaryl and mixtures thereof, and wherein $R_4$ or $R_7$ are not both hydrogen.

2. The process of claim 1, wherein the at least one compatibility agent has a normal boiling point exceeding about 185° C.

3. The process of claim 1, wherein the at least one compatibility agent is present in an amount effective to increase the loading of the second hydrocarbon compound in the second stream, as compared with extractive distillation in the absence of the compatibility agent.

4. The process of claim 1, wherein the extractive distillation composition further comprises dimethylsulfone.

5. The process of claim 1, wherein the extractive distillation composition further comprises water.

6. The process of claim 1, wherein the first hydrocarbon compound comprises at least one saturated hydrocarbon residue, and the second hydrocarbon compound comprises at least one carbon-carbon double bond.

7. The process of claim 1, wherein the first hydrocarbon compound is a $C_7$–$C_{10}$ aliphatic compound.

8. The process of claim 1, wherein the second hydrocarbon compound comprises an aromatic residue.

9. The process of claim 1, wherein the second hydrocarbon compound is a $C_6$–$C_{10}$ substituted benzene compound.

10. The process of claim 1, wherein the second hydrocarbon compound is benzene, toluene, ortho-xylene, meta-xylene, para-xylene, or a mixture thereof.

11. The process of claim 1, wherein the first and/or second hydrocarbon compounds form an azeotropic mixture.

12. The process of claim 1, wherein the first and second hydrocarbon compounds have normal boiling points that differ by less than 5° C.

13. The process of claim 1, wherein the feed mixture comprises a mixture of aliphatic and aromatic compounds.

14. The process of claim 1, wherein the feed mixture is a BTX stream.

15. The process of claim 1, comprising further treating the second stream to separate the second hydrocarbon compound from the extraction distillation composition.

16. A process for separating hydrocarbon compounds of similar boiling points by extractive distillation, comprising the steps of:
   a. introducing a feed mixture into an extractive distillation zone having an upper portion and a lower portion, wherein the feed mixture comprises at least
      i. a first hydrocarbon compound comprising a C7–C10 aliphatic compound, and
      ii. a second hydrocarbon compound comprising benzene, toluene, ortho-xylene, meta-xylene, para-xylene, or a mixture thereof; and
   b. introducing an extractive distillation composition into the upper portion of the extractive distillation zone; and
   c. distilling the feed mixture to at least partially separate the feed mixture into a first stream rich in the first hydrocarbon compound, and a second stream rich in the second hydrocarbon compound;
   wherein the extractive distillation composition comprises:
      i. about 100 parts by weight of at least one alkylene glycol, and
      ii. from about 5 to about 35 parts by weight of a compatibility agent or a mixture of compatibility agents, wherein the compatibility agent comprises 2-ethyl-1-hexanol, dipropylene glycol methyl ether acetate, 1-octanol, 1-tridecanol, oleyl alcohol, 1-decanol (decyl alcohol), ethylene glycol dibutyrate, 1,2-decane carbonate, 1,2-dodecane carbonate, N-(2-aminoethyl)piperazine, aniline, 1,2-butylene carbonate, isobutyl heptyl ketone, dimethyl adipate, dimethyl glutarate, dimethylsuccinate, di-n-butyl sebacate, o-dichlorobenzene, diethyl succinate, diisobutylcarbinol, ethylene glycol butyl ether, ethyl decanoate, 2-ethylhexyl acetate, a hexyl acetate, a heptyl acetate, an octyl acetate, a nonyl acetate, a decyl acetate, N-formyl morpholine, hexamethylphosphoramide, 1,2-hexane carbonate, 1-isopropyl-2-methyl imidazole, 3-isopropyl-2-oxazolidinone, methoxyisopropyl acetamide, methoxyisopropyl formamide, methoxypropyl acetamide, methoxypropy formamide, methyl oleate, nonylphenol, 2-octanol, propylene glycol diacetate, pine oil, iso-propyl palmitate, alpha-terpineol, tri-n-butyl phosphate, acetophenone, benzonitrile, di-n-butyl phthalate, diethyl phthalate, dimethyl phthalate, ethyl cinnamate, isophorone, nitrobenzene, or quinoline.

17. The process of claim 16, wherein the extractive distillation composition further comprises dimethylsulfone.

18. The process of claim 16, wherein the extractive distillation composition further comprises water.

19. A process for separating a mixture of hydrocarbon compounds by extractive distillation that employs an extractive distillation composition, wherein the improvement comprises the use of a mixture comprising at least one alkylene glycol compound, and at least one compatibility agent, wherein the at least one compatibility agent:

a. has a Hansen's Solubility Polar Parameter from about 2.7 to about 6.4 (calories/cm$^3$)$^{1/2}$, and a Hansen's Solubility Hydrogen Bonding Parameter from about 1.0 to about 4.4 (calories/cm$^3$)$^{1/2}$;

b. has a boiling point higher than the boiling point of the mixture of hydrocarbon compounds; and c. does not comprise
  i. an N-hydrocarbyl-substituted pyrrolidone compound or residue, or an N-hydrocarbyl-substituted-2-thiopyrrolidone compound or residue, or
  ii. a polyalkyleneglycol ether compound of the formula:

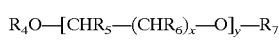

wherein $R_4$, $R_5$, $R_6$ and $R_7$ may be hydrogen alkyl, aryl, aralkyl, alkylaryl and mixtures thereof, and wherein $R_4$ or $R_7$ are not both hydrogen.

20. The process of claim 19, further comprising dimethylsulfone.

21. The process of claim 1, wherein the compatibility agent has a Hansen's Solubility Polar Parameter from about 3.2 to about 5.9 (calories/cm$^3$)$^{1/2}$, and a Hansen's Solubility Hydrogen Bonding Parameter from about 1.5 to about 3.9 (calories/cm$^3$)$^{1/2}$.

22. The process of claim 19, wherein the compatibility agent has a Hansen's Solubility Polar Parameter from about 3.2 to about 5.9 (calories/cm$^3$)$^{1/2}$, and a Hansen's Solubility Hydrogen Bonding Parameter from about 1.5 to about 3.9 (calories/cm$^3$)$^{1/2}$.

23. The process of claim 1, wherein the compatibility agent comprises a substituted or unsubstituted derivative of:

a. a dialkyl phthalate ester,
b. a cinnamate ester,
c. a C6–C12 alkyl ester of acetic, propionic, or butyric acid,
d. a C7–C10 methyl-alkyl ketone,
e. a dialkylester of succinic, glutaric, adipic or sebacic acids, or a mixture thereof,
f. a $C_8$–$C_{18}$ saturated or unsaturated acyclic alcohol,
g. a $C_4$–$C_{12}$ alkylene carbonate,
h. an alkoxypropyl or alkoxyisopropyl derivative of formamide or acetamide,
i. a methyl or ethyl ester of a $C_{10}$–$C_{18}$ carboxylic acid,
j. an amino-, nitro-, cyano-, acetyl-, and dichloro- derivative of benzene, or
k. a polyalkylene glycol diester, or monoether ester.

24. The process of claim 19, wherein the compatibility agent comprises a substituted or unsubstituted derivative of:

a. a dialkyl phthalate ester,
b. a cinnamate ester,
c. a C6–C12 alkyl ester of acetic, propionic, or butyric acid,
d. a C7–C10 methyl-alkyl ketone,
e. a dialkylester of succinic, glutaric, adipic or sebacic acids, or a mixture thereof,
f. a $C_8$–$C_{18}$ saturated or unsaturated acyclic alcohol,
g. a $C_4$–$C_{12}$ alkylene carbonate,
h. an alkoxypropyl or alkoxyisopropyl derivative of formamide or acetamide,
i. a methyl or ethyl ester of a $C_{10}$–$C_{18}$ carboxylic acid,
j. an amino-, nitro-, cyano-, acetyl-, and dichloro- derivative of benzene, or
k. a polyalkylene glycol diester, or monoether ester.

25. The process of claim 1, wherein the compatibility agent comprises one or more of 2-ethyl-1-hexanol, dipropylene glycol methyl ether acetate, 1-octanol, 1-tridecanol, oleyl alcohol, 1-decanol (decyl alcohol), ethylene glycol dibutyrate, 1,2-decane carbonate, 1,2-dodecane carbonate, N-(2-aminoethyl)piperazine, aniline, 1,2-butylene carbonate, isobutyl heptyl ketone, dimethyl adipate, dimethyl glutarate, dimethylsuccinate, di-n-butyl sebacate, o-dichlorobenzene, diethyl succinate, diisobutylcarbinol, ethylene glycol butyl ether, ethyl decanoate, 2-ethylhexyl acetate, a hexyl acetate, a heptyl acetate, antoctyl acetate, a nonyl acetate, a decyl acetate, N-formyl morpholine, hexamethylphosphoramide, 1,2-hexane carbonate, 1-isopropyl-2-methyl imidazole, 3-isopropyl-2-oxazolidinone, methoxyisopropyl acetamide, methoxyisopropyl formamide, methoxypropyl acetamide, methoxypropy formamide, methyl oleate, nonylphenol, 2-octanol, propylene glycol diacetate, pine oil, iso-propyl palmitate, alpha-terpineol, tri-n-butyl phosphate, acetophenone, benzonitrile, di-n-butyl phthalate, diethyl phthalate, dimethyl phthalate, ethyl cinnamate, isophorone, nitrobenzene, or quinoline.

26. The process of claim 19, wherein the compatibility agent comprises one or more of 2-ethyl-1-hexanol, dipropylene glycol methyl ether acetate, 1 -octanol, 1-tridecanol, oleyl alcohol, 1-decanol (decyl alcohol), ethylene glycol dibutyrate, 1,2-decane carbonate, 1,2-dodecane carbonate, N-(2-aminoethyl)piperazine, aniline, 1,2-butylene carbonate, isobutyl heptyl ketone, dimethyl adipate, dimethyl glutarate, dimethylsuccinate, di-n-butyl sebacate, o-dichlorobenzene, diethyl succinate, diisobutylcarbinol, ethylene glycol butyl ether, ethyl decanoate, 2-ethylhexyl acetate, a hexyl acetate, a heptyl acetate, an octyl acetate, a nonyl acetate, a decyl acetate, N-formyl morpholine, hexamethylphosphoramide, 1,2-hexane carbonate, 1-isopropyl-2-methyl imidazole, 3-isopropyl-2-oxazolidinone, methoxyisopropyl acetamide, methoxyisopropyl formamide, methoxypropyl acetamnide, methoxypropy formamide, methyl oleate, nonylphenol, 2-octanol, propylene glycol diacetate, pine oil, iso-propyl palmitate, alpha-terpineol, tri-n-butyl phosphate, acetophenone, benzonitrile, di-n-butyl phthalate, diethyl phthalate, dimethyl phthalate, ethyl cinnamate, isophorone, nitrobenzene, or quinoline.

* * * * *